J. A. SHERMAN.

Trusses.

No. 4,697. Reissued Jan. 2, 1872.

Witnesses.

Chas. A. Smith

Harold Ferrell

Inventor.

J. A. Sherman,

Lemuel W. Serrell

Att'y.

AM. PHOTO-LITHOGRAPHIC CO. N.Y. (OSBORNE'S PROCESS.)

UNITED STATES PATENT OFFICE.

JACOB A. SHERMAN, OF NEW YORK, N. Y.

IMPROVEMENT IN TRUSSES.

Specification forming part of Letters Patent No. 55,724, dated June 19, 1866; reissue No. 4,697, dated January 2, 1872.

*To all whom it may concern:*

Be it known that I, JACOB A. SHERMAN, of the city and State of New York, have invented, made, and applied to use a certain new and useful Improvement in Trusses; and I do hereby declare the following to be a full, clear, and exact description of the said invention, reference being had to the annexed drawing making part of this specification, wherein—

Figure 1:
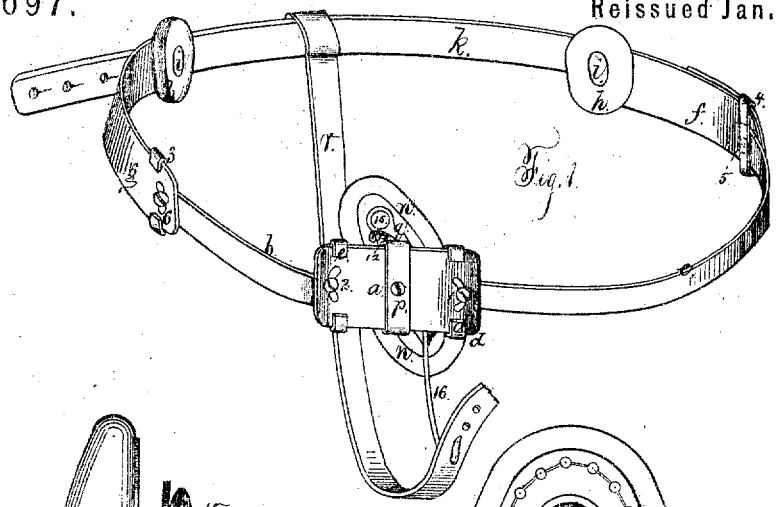
Figure 4:
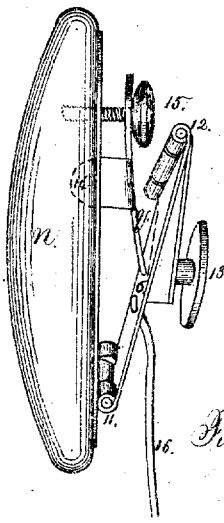
Figure 5:
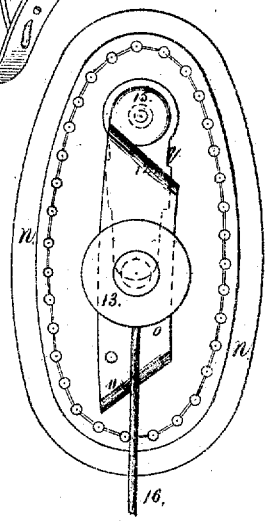
Figure 6:
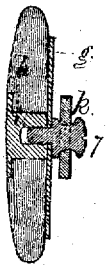
Figure 2:
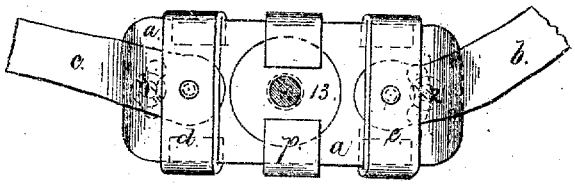
Figure 3:
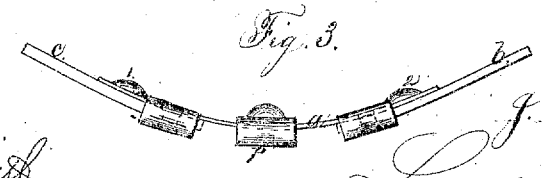

Figure 1 is a perspective view of the improved truss. Fig. 2 is a back view of the pressure-spring of the truss. Fig. 3 is a plan of said pressure-spring. Fig. 4 is a side view, and Fig. 5 is a view of the back of the hernial pad. Fig. 6 is a section of the pressure-buttons or pads at the ends of the truss-springs.

The nature of my invention consists in a pressure-spring between two rigid curved bars, which spring is curved so as to produce a pressure toward the person to hold the pad to the hernia, and at the outer ends of the bars are curved springs to clasp the hips, having peculiar pressure-buttons at their ends. The springs and bars are adjustable so as to stand at the desired angle toward each other, and the pad is constructed so as to give pressure at the upper or lower portion of the pad, as may be required for the hernia.

In the drawing, *a* is my pressure-spring, curved inward. *b* and *c* are curved metal bars, attached at their ends by rivets to the clips *d* and *e*, that slip over the spring *a*; and 1 and 2 are screws passing through segmental slots in the spring *a* for securing the bars firmly at any angle at which they may be placed, so as to accommodate the shape of the person or the position of the hernia. The ends of the arms *b* and *c* are fitted with curved hip-springs *f* and *g*, attached by the clips 3 and 4 and screws 5 and 6, in segmental slots similar to those in the plate *a*, so that the springs *f* and *g* can be placed on the line of or at an angle to the bars *b* and *c*. At the ends of the springs *f* and *g* are the pressure-buttons or pads *h h*, formed of hard rubber or other material, and each of these has in it a flanged nut, *i*, introduced from the inside and receiving the button-screw 7, (see Fig. 6,) passing through a hole in the spring *g* or *f*, so as to hold the button *h* firmly in place and at the same time present to the body of the wearer a smooth surface that will not produce any injury or irritation, as sometimes arises from the point of a screw coming through the pad. The back-strap *k* extends from one of the button-heads 7 to the other, to aid in holding the truss to place. It may, however, be sometimes worn without this back-strap *k*. The hernial pad *n* is formed upon a plate, at the back of which is a double-hinged attachment by which pressure may be given, either at the top or the bottom of the pad. Upon the plate of this pad a hinge, 11, is formed connecting the lever-plate *o*, and at the outer end of the plate *o* is a second hinge, 12, for a plate carrying the button 13, which button is received and secured by the clip *p* and its set-screw to the spring *a*. *q* is a lever on a fulcrum, 14, at one end of which is a screw, 15. The other end takes beneath the lever *o*. 16 is a lever-arm extending from *o* and provided with a hook at its end. The hinges 11 and 12 are placed diagonally, as seen in Fig. 5; hence the pad *n* will not move on the hinges at right angles to the spring *a*, but when applied to the person will conform to the shape of the body at the groin as it is pressed inward upon a hernia. The pad *n* is to be placed in the proper position over the hernia before the clip *p* is tightened by its set-screw. If pressure is desired mostly at the bottom of the pad the strap *r* from the back-strap *k* is hooked over the arm 16, and the hinge 12 becomes the point of motion for the pad, and it is pressed inward and upward at the bottom. If the pressure is to be given at the top of the pad the screw 15 is screwed in, which by the lever *q* increases the distance between the hinge 12 and pad *n*. The lever *o* moving upon the hinge 11 throws the pad in at the upper end and right-hand edge (to the wearer) so as to press upon a hernia and at the same time conform to the shape of the groin. One of the inclined hinges 11 or 12 might be dispensed with if it is desired that only the top or the bottom of the pad be pressed inward.

It will be evident that the pads may be applied on the left side of the person or according to the position of the hernia, the instrument being constructed accordingly, and in cases where there is a rupture on both sides a second plate, *a*, and pad may be introduced, the bar *c* being divided for that purpose.

The springs *f* and *g* may be made of single leaves, of any desired length or strength, or two or more leaves may be employed, as shown in the spring *f*, and the spring *a* may also be made with two or more leaves.

I claim as my invention—

1. The curved pressure-spring *a*, introduced between and united to the separate rigid bars *b* and *c*, and carrying the truss-pad, as specified.

2. The connecting-spring *a* and rigid bars *b* and *c*, carrying the truss-pad as aforesaid, in combination with segmental slots and clamping-screws for retaining the bars *b* and *c* in their proper relative position to the spring *a*, as set forth.

3. The inclined hinge (11 or 12) for uniting the pad to the truss-spring *a* so as to allow the adjustment of the pad, as specified.

4. The lever *q* and screw 15, in combination with the lever *o* and diagonal hinges 11 and 12, as and for the purposes set forth.

5. The separate adjustable curved hip-springs *f g*, in combination with the bars *b* and *c* and spring *a*, for retaining said bars *b c*, spring *a*, and pad in position, as set forth.

Signed by me this 25th day of July, A. D. 1871.

J. A. SHERMAN.

Witnesses:
CHAS. H. SMITH,
GEO. T. PINCKNEY.

(156)